US011721434B2

(12) United States Patent
Hirst et al.

(10) Patent No.: US 11,721,434 B2
(45) Date of Patent: Aug. 8, 2023

(54) INTELLIGENT PATIENT MONITOR MOUNT

(71) Applicant: DRÄGERWERK AG & CO. KGAA, Lübeck (DE)

(72) Inventors: Michael D. Hirst, Webster, MA (US); Joshua Abell, Beverly, MA (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 332 days.

(21) Appl. No.: 15/533,644

(22) PCT Filed: Nov. 30, 2015

(86) PCT No.: PCT/US2015/062987
§ 371 (c)(1),
(2) Date: Jun. 6, 2017

(87) PCT Pub. No.: WO2016/099844
PCT Pub. Date: Jun. 23, 2016

(65) Prior Publication Data
US 2017/0364651 A1    Dec. 21, 2017

Related U.S. Application Data

(60) Provisional application No. 62/093,961, filed on Dec. 18, 2014.

(51) Int. Cl.
*G16H 40/63* (2018.01)
*G16H 40/67* (2018.01)
(52) U.S. Cl.
CPC ............ *G16H 40/63* (2018.01); *G16H 40/67* (2018.01)

(58) Field of Classification Search
CPC ...... G06F 19/3419; G06F 13/38; G06F 13/00; G06F 19/00; G16H 40/63; G16H 40/20;
(Continued)

(56) References Cited

U.S. PATENT DOCUMENTS 5,640,953 A * 6/1997 Bishop ................ G06F 19/3418
600/300
5,687,717 A 11/1997 Halpern et al.
(Continued)

FOREIGN PATENT DOCUMENTS

WO 2008/083285 A1 7/2008

OTHER PUBLICATIONS

Freescale Home Health Hub wants to usher in the era of connected medical devices, Retrieved from the internet URL: https://www.engadget.com/2011/11/19/freescalehomehealthhubwantstousherintheeraofconnected, AOL, Inc., 11 pages (2017).
(Continued)

*Primary Examiner* — Fonya M Long
*Assistant Examiner* — Alaaeldin M Elshaer
(74) *Attorney, Agent, or Firm* — Nolte Lackenbach Siegel

(57) ABSTRACT

Data that is derived from a medical device connected to or communicating with, a patient monitor mount, is detected by the patient monitor mount. The data is monitored for events associated with the medical device. The patient monitor mount then determines that the monitored event corresponds to an event. The patient monitor mount generates at least one command for a visualization device to change the data displayed on the visualization device. The command is then transmitted to the visualization device. Related apparatus, systems, methods and articles are also described.

25 Claims, 7 Drawing Sheets

(58) Field of Classification Search
CPC .......... G06Q 50/00; G06Q 50/24; A61B 5/00; A61B 5/08; A61B 6/00; G08B 1/08
USPC .......................................... 705/2, 3; 710/62
See application file for complete search history.

(56) References Cited

U.S. PATENT DOCUMENTS

| | | | |
|---|---|---|---|
| 6,183,417 B1 | 2/2001 | Geheb et al. | |
| 8,405,608 B2 * | 3/2013 | Al-Ali | A61B 5/0002 345/158 |
| 2005/0033124 A1 | 2/2005 | Kelly et al. | |
| 2007/0271115 A1 * | 11/2007 | Baldus | G06Q 50/22 705/2 |
| 2008/0183910 A1 * | 7/2008 | Natoli | A61B 5/00 710/15 |
| 2010/0274098 A1 * | 10/2010 | Belford | G16H 40/63 600/300 |
| 2011/0105854 A1 * | 5/2011 | Kiani | G06F 19/00 600/300 |
| 2012/0317327 A1 * | 12/2012 | Eaton | A61B 5/0002 710/303 |
| 2013/0045685 A1 * | 2/2013 | Kiani | G08B 21/24 455/41.2 |
| 2013/0262730 A1 | 10/2013 | Al-Ali et al. | |
| 2014/0085078 A1 * | 3/2014 | Carnes | A61B 5/7465 340/539.12 |
| 2015/0097701 A1 * | 4/2015 | Al-Ali | A61B 5/0002 340/870.07 |

OTHER PUBLICATIONS

Patent Cooperation Treaty, International Search Report and Written Opinion for Application No. PCT/US2015/062987, dated Mar. 10, 2016.
GE Healthcare, "DASH 3000/4000/5000 (TM) Patient Monitor Service Manual," Apr. 22, 2013. Retrieved from the Internet: URL:http://www3.gehealthcare.com/~/media/downloads/us/services/equipmentservices/support-center/daylight-savings-time/patient-monitoring/monitors/gehc-service-manual-dash-3000-4000-5000-patient-monitor_v7.pdf, retrieved on Mar. 1, 2016 (282 pages).
Patent Cooperation Treaty, International Preliminary Report on Patentability for PCT/US2015/062987, dated Jun. 29, 2017.

* cited by examiner

INTELLIGENT PATIENT MONITOR MOUNT

CROSS REFERENCE TO RELATED APPLICATIONS

The current application is a national stage application, filed under 35 U.S.C. § 371, of International Application No PCT/US2015/062987, filed Nov. 30, 2015, which claims priority to U.S. Pat. App. Ser. No. 62/093,961 filed on Dec. 18, 2014, the entire contents of which are hereby fully incorporated by reference.

TECHNICAL FIELD

The subject matter described herein relates to medical devices, in particular, to mounts for patient monitors.

BACKGROUND

Patient monitors are used by health care facilities to monitor and display information about a patient, e.g. vital signs, status of connected devices, etc. Patient monitors typically are portable devices that travel with the patient in order to provide continuous monitoring during care. When a patient arrives at a hospital room or other treatment location, the patient monitor is often plugged into or otherwise connected to a patient monitor mount. Patient monitor mounts provide a physical interface for the patient monitor and are generally fixed to the treatment location. Patient monitor mounts also provide electrical connection to other devices or infrastructure, e.g. power to recharge patient monitor batteries, network connectivity to other medical devices or hospital computer systems, etc.

SUMMARY

In a first aspect, data that is derived from a medical device connected to or communicating with, a patient monitor mount, is detected by the patient monitor mount. The data is monitored for events associated with the medical device. The patient monitor mount then determines that the monitored event corresponds to an event. The patient monitor mount generates at least one command for a visualization device to change the data displayed on the visualization device. The command is then transmitted to the visualization device.

In a further interrelated aspect, there can be electronic communication between a patient monitor and the patient monitor mount, where the patient monitor displays data derived from coupled medical devices.

In yet another interrelated aspect, the command can cause a visualization in the data displayed on the patient monitor to change.

In some variations, the event can be described by a rule set in a visualization configuration. The rule set can describe rules related to events and the patient monitor uses the rule set to generate the command. The command can be an HTML command.

In other variations, the visualization can be triggered based on a device rule set, a phase rule set, and/or an event rule set.

In further variations, the event can be an additional medical device being coupled to, or initiating communication with, the patient monitor mount. In addition or in the alternative, the event can be a change in phase of a medical procedure and/or an occurrence of an alert.

In yet another variation, the visualization configuration can include a list, priority information, positions, and display preferences of diagnostic traces displayed on the patient monitor or visualization device. The data displayed can also be replicated on a display of a computer connected to a network. The connection can be wired or wireless.

In another variation, the patient monitor mount can further include a doc connector that enables a mechanical and electrical connection between the patient monitor and the patient monitor mount. There can be a power supply to provide power to the patient monitor mount. A pod expansion port can be connected to the dock connector. There can be a registered jack connected to the doc connector to enable internet communication with the patient monitor mount. There can be an RFID and WiFi interface to enable RF and wireless communication. There can also be an Ethernet switch, a random-access memory, a persistent memory, and a microprocessor.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

Implementations of the current subject matter can provide one or more advantages. For example, the patient monitor mount provides upgraded functionality to the patient monitor. Specifically, allowing preconfigured display settings that cause the patient monitor to display custom diagnostic screen sets. Also, by using a rule set, the patient monitor mount can change what is displayed on the patient monitor in anticipation of, or in reaction to, patient events.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a patient monitor mount, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

The current subject matter is directed to methods, systems, apparatus, articles/computer program products for displaying dynamic or customizable patient diagnostics on a patient monitor. In particular, a patient monitor mount provides a unique clinical display generation capability. The clinical display is automatically generated by monitoring the medical device data on the hospital network. The displayed data can also be configured by caregivers to be customized to the status of medical devices connected to the patient, or to other events. The images from the clinical display can also or alternatively be displayed as a webview by any networked device capable of displaying webpages.

Figure 1A:
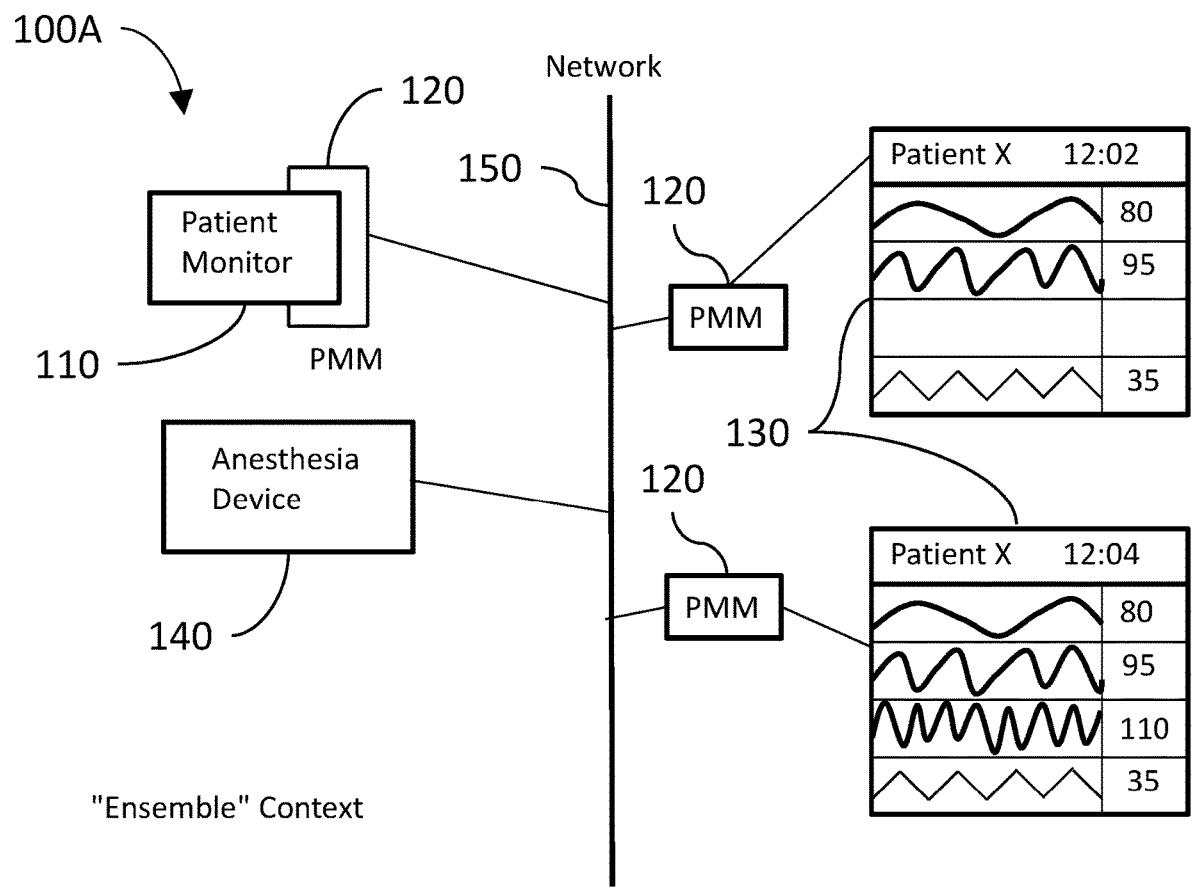
FIGS. 1A-C are diagrams illustrating a patient monitor, connected to a patient monitor mount, displaying context-based data.
Figure 1B:
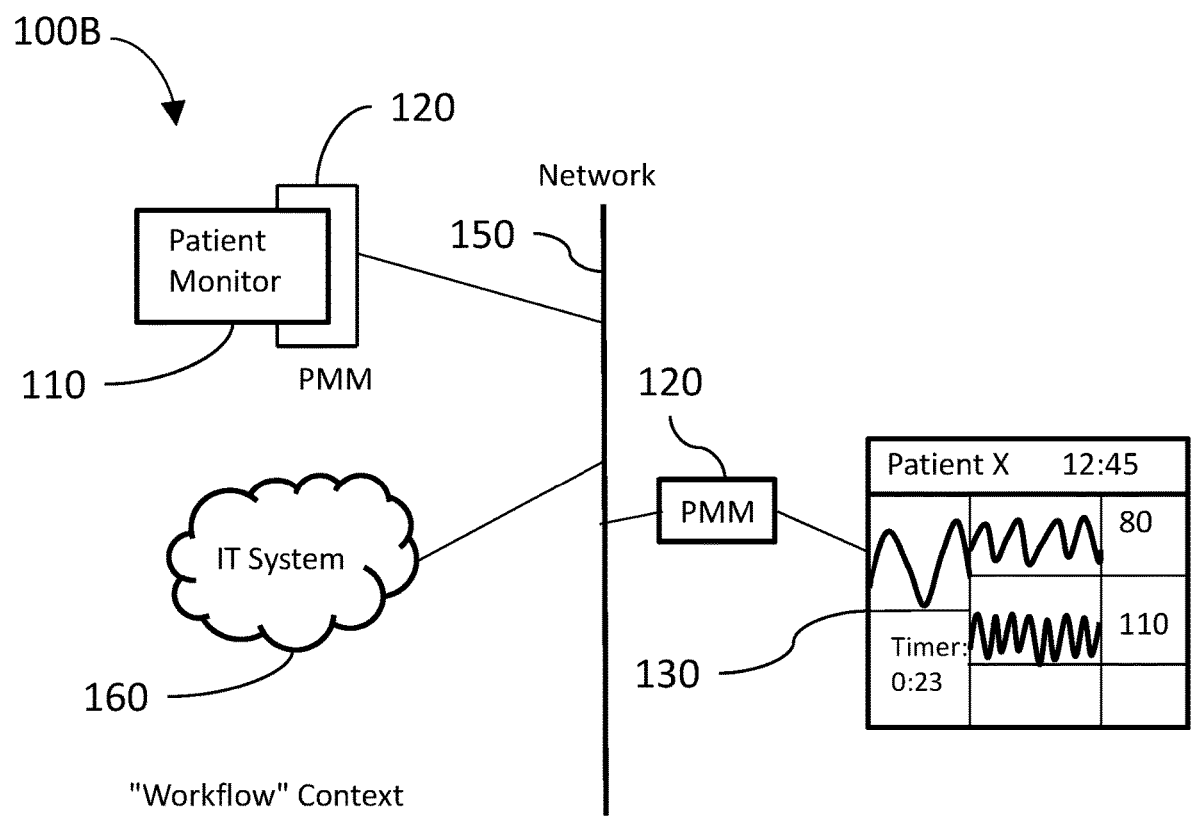
Figure 1C:
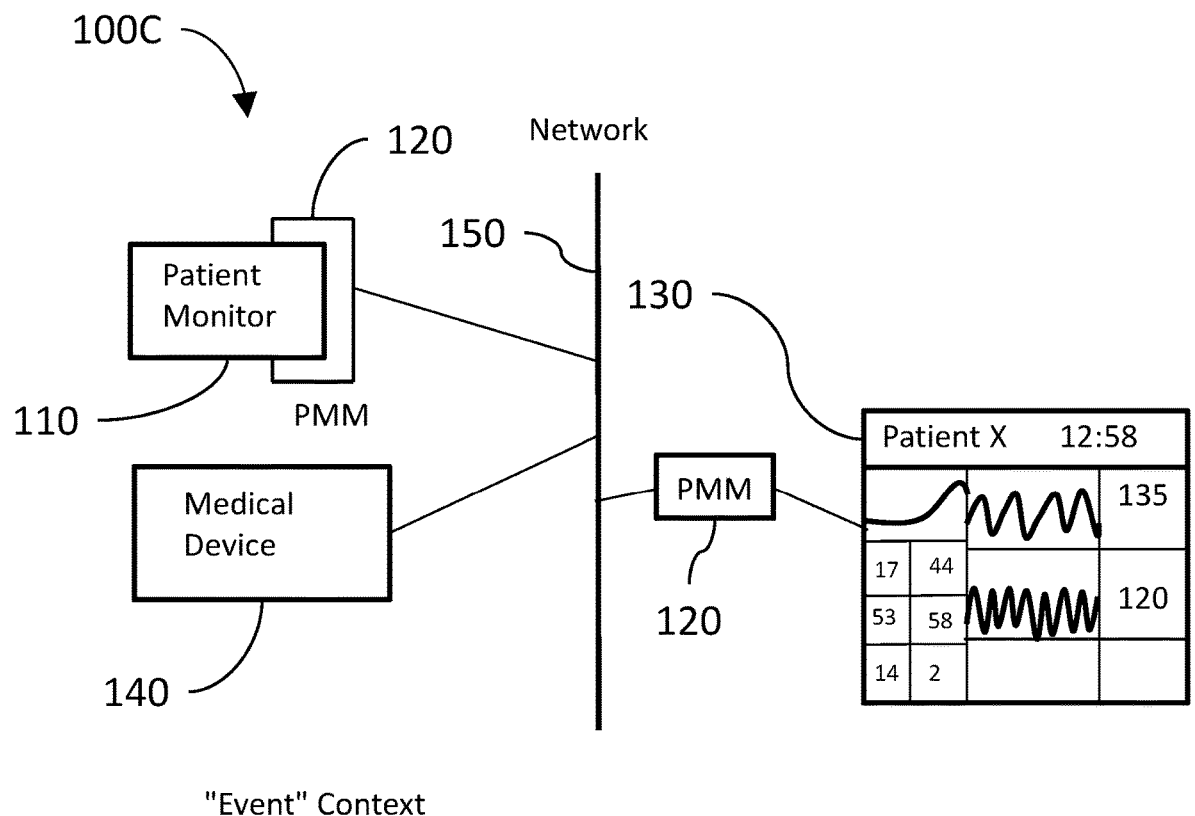

FIGS. 1A-C are diagrams 100A-C illustrating a patient monitor 110, connected to a patient monitor mount 120, displaying context-based data 130. The patient monitor mount 120 provides functionality to the patient monitor 110 that allows the patient monitor 110 to display data related to the status of medical devices 140 connected to the patient or in response to patient events. There can be several kinds of contexts, or modes of use, for the patient monitor mount 120 that change the data 130 depending on what is occurring with the patient. For example, there can be an "ensemble" context, a "workflow" context, and an "event" context.

The ensemble context can relate to the patient monitor mount 120 detecting changes in the status of an ensemble of connected medical devices 140 and updating the data 130 of the patient monitor 110. For example, as shown in diagram 100A of FIG. 1A, the patient monitor 110 can be mounted on the patient monitor mount 120, enabling electronic communication between the patient monitor 110 and the patient monitor mount 120. The patient monitor 110 can be any sort of patient monitoring device that can be used to monitor the vital signs/wellbeing or medical device 140 data 130 associated with a patient.

In another implementation, the patient monitor mount 120 need not be connected to a patient monitor. Here, the patient monitor mount 120 can detect data derived from medical devices 140 that are in communication with the patient monitor mount 120. The patient monitor mount 120 can perform functions, described in greater detail below, to display data on connected visualization devices.

Figure 3:
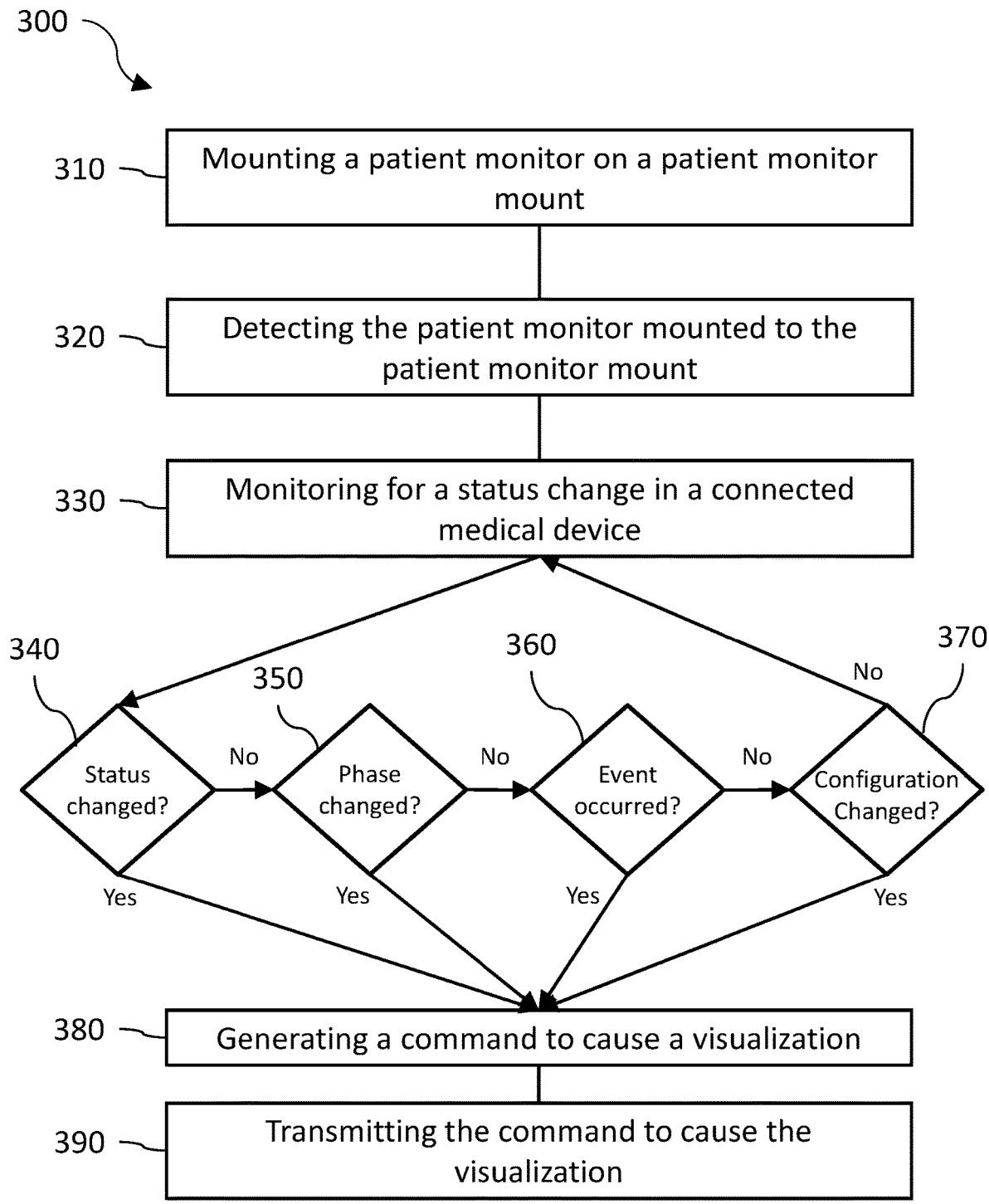
FIG. 3 is a process flow diagram illustrating the data of the patient monitor being updated by the patient monitor mount.

The patient monitor mount 120 can be a physical docking station, described in more detail in FIG. 3, which connects the patient monitor 110 to the systems of the patient care facility. Once mounted, it can be detected that the patient monitor 110 is mounted to the patient monitor mount 120.

Once detected, data 130 can be displayed on the patient monitor 110. The data 130 can include, e.g. diagnostic traces from associated medical devices 140, patient information, timers, readouts, images, etc. The data 130 can be based on a visualization configuration that is already present in the patient monitor 110, the patient monitor mount 120, or a networked computer. The data 130 can be updated in response to a number of scenarios, including e.g. moving the patient, starting a new procedure, updating the visualization configuration, connecting other medical devices to the patient, etc. For example, in FIG. 1A, after the medical device 140 (in this case an anesthesia device) has been connected to the patient and the network, the patient monitor mount 120, according to its visualization configuration, updates the data 130 displayed to create a visualization of the updated data. The updated data 130 differs from the prior data 130 in that it includes a diagnostic trace relating to the newly connected medical device 140. The detection of medical devices 140 and the updating of the patient monitor 110 can be performed by either the patient monitor mount 120 or by a networked computer connected to the patient monitor mount 120. The patient monitor 110 and the patient monitor mount 120 can be connected to a network 150, discussed further below, to enable sharing and configuring of data 130 by various users.

The workflow context as illustrated in diagram 100B of FIG. 1B can describe the data 130 of the patient monitor 110 being updated according to structured events, i.e. phases. As the patient is treated, the treatment may require the patient to be moved to different locations in the treatment facility. As the patient is moved from location to location, the patient monitor 110 is mounted on the patient monitor mount 120 at each location, which can then update the data 130 of the patient monitor 110 to reflect the visualization configuration at the new location. Another function of the patient monitor mount 120 can be to update the data 130 of the patient monitor 110 according to phases of an operation or procedure or series of procedures. For example, a surgeon may desire a specific set of data to be displayed during the initial phase of a heart transplant operation, and a different set of data to be displayed when the patient is on a cardiopulmonary bypass machine. This functionality can be programmed into the visualization configuration of the patient monitor mount 120 by interfacing an information technology (IT) system 160 with the patient monitor mount 120. The IT system 160 can include any number of networked computers, servers, databases, etc. needed to manage the visualization configurations used by the patient monitor mounts 120. One implementation of the IT system 160 is described in FIG. 5.

The event context as illustrated in diagram 100C of FIG. 1C can describe the data 130 of the patient monitor 110 being updated according to unplanned events during patient monitoring. For example, the medical device 140 connected to the patient detects an emergency situation. In addition to sending out an alert, the patient monitor mount 120 can update the data 130 of the patient monitor 110 to display specific data 130 that is needed by caregivers to address the emergency.

Figure 2:
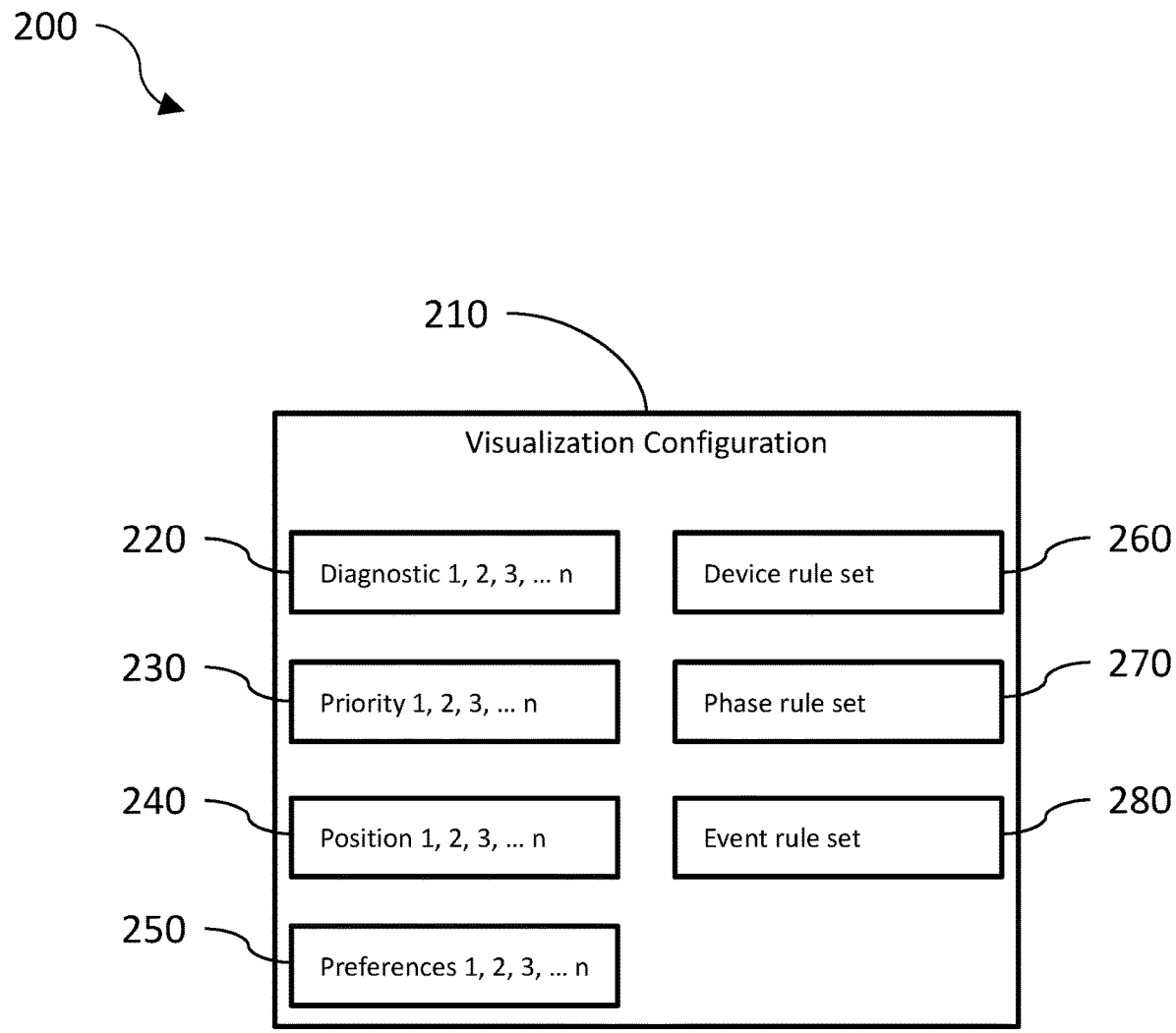
FIG. 2 is a block diagram illustrating a visualization configuration used by the patient monitor mount.

FIG. 2 is a block diagram 200 illustrating the visualization configuration 210 used by the patient monitor mount 120. The visualization configuration 210 used by the patient monitor mount 120 can include a list 220 of diagnostics (or diagnostic traces), e.g. respirator, anesthesia device, etc. The visualization configuration 210 can also include the priority 230 with which to display the diagnostics, i.e. if a choice has to be made between diagnostics to display, which one is more important. There can also be the position 240 of the diagnostics, e.g. first, last, upper left, X-Y coordinates, etc. Also, other preferences 250 can be included, e.g. color, range, scale, refresh rate, etc.

The visualization configuration 210 can also include rule sets to govern events in different contexts, as described above. The visualizations can be triggered by the rule sets in response to events. There can be a device rule set 260 that can display a particular data 130 for one medical device 140, and another data 130 for another medical device 140. The device rule set 260 can also govern which medical devices 140 to display data 130 for in the event of a conflict, e.g. too many medical devices 140 connected, etc. There can be a phase rule set 270 that governs displaying data 130 depending on what phase of a procedure is taking place, e.g. where the patient is in the treatment facility, what the current condition of the patient is, etc. There can also be an event rule set 280 that describes what diagnostics are to be displayed on the patient monitor 110 in response to different events. This can include emergency events, where critical information can be automatically displayed as the data 130. The event rule set 280 can handle situations where the caregiver may not have the time to reprogram the patient monitor 110 to display needed information.

The visualization configuration 210 can also be a combination of user-defined input and predefined input. For example, if during a procedure, the medical device 140 determines that a particular diagnostic trace should be viewed, it can be displayed in an unused frame, presented as a pop-up window, or resizing/reformatting the data 130 so as to display the new information, but without removing information that may have been manually configured by the caregiver.

FIG. 3 is a process flow diagram illustrating the data 130 of the patient monitor 110 being updated by the patient monitor mount 120. At 310, the patient monitor can be mounted to the patient monitor mount.

At 320, the patient monitor mount 120 can detect that the patient monitor 110 has been mounted and that electronic communication has been enabled between the patient monitor 110 and the patient monitor mount 120. The patient monitor 110 can display data 130 derived from the medical device 140 connected to the patient monitor.

At 330, the patient monitor mount 120, after detecting the patient monitor 110, can monitor for an event associated with the connected medical device 140.

A number of checks, queries, etc. can be performed either manually or automatically, to determine if the data 130 needs to be updated. The patient monitor mount 120 can determine that the monitored event corresponds to a rule in the rule set in the visualization configuration 210.

At 340, a query can be made to determine if the status of one or more medical devices 140 have changed such that, according to the device rule set 260, the data 130 should be updated.

At 350, a query can be made to determine if the phase has changed such that, according to the phase rule set 270, the data 130 should be updated.

At 360, a query can be made to determine if an event has occurred such that, according to the event rule set 280, the data 130 should be updated.

At 370, a query can be made to determine if the visualization configuration 210 has changed such that, according to the new visualization configuration 210, the data 130 should be updated.

At 380, if any of the conditions in 340, 350, 360, or 370 were true, then a command can be generated by the patient monitor mount 120 using the rule set. The command, when received by the patient monitor 110, causes a visualization in which the data 130 displayed on the patient monitor mount 120 changes. The command can be in any computer language or format, e.g. HTML, JAVA, C, C++, etc. If the conditions in 340, 350, 360, and 370 were not true, then the patient monitor 110 can continue to display the current data 130.

In another implementation, there can be a visualization device, which can be the patient monitor 110, but can also be any other type of device capable of generating the visualization, e.g. a terminal, wall monitor, mobile device, desktop monitor, dedicated LCD display, etc. At 390, the command can be transmitted by the patient monitor mount 120 to the patient monitor 110 and/or to the visualization device.

Figure 4:
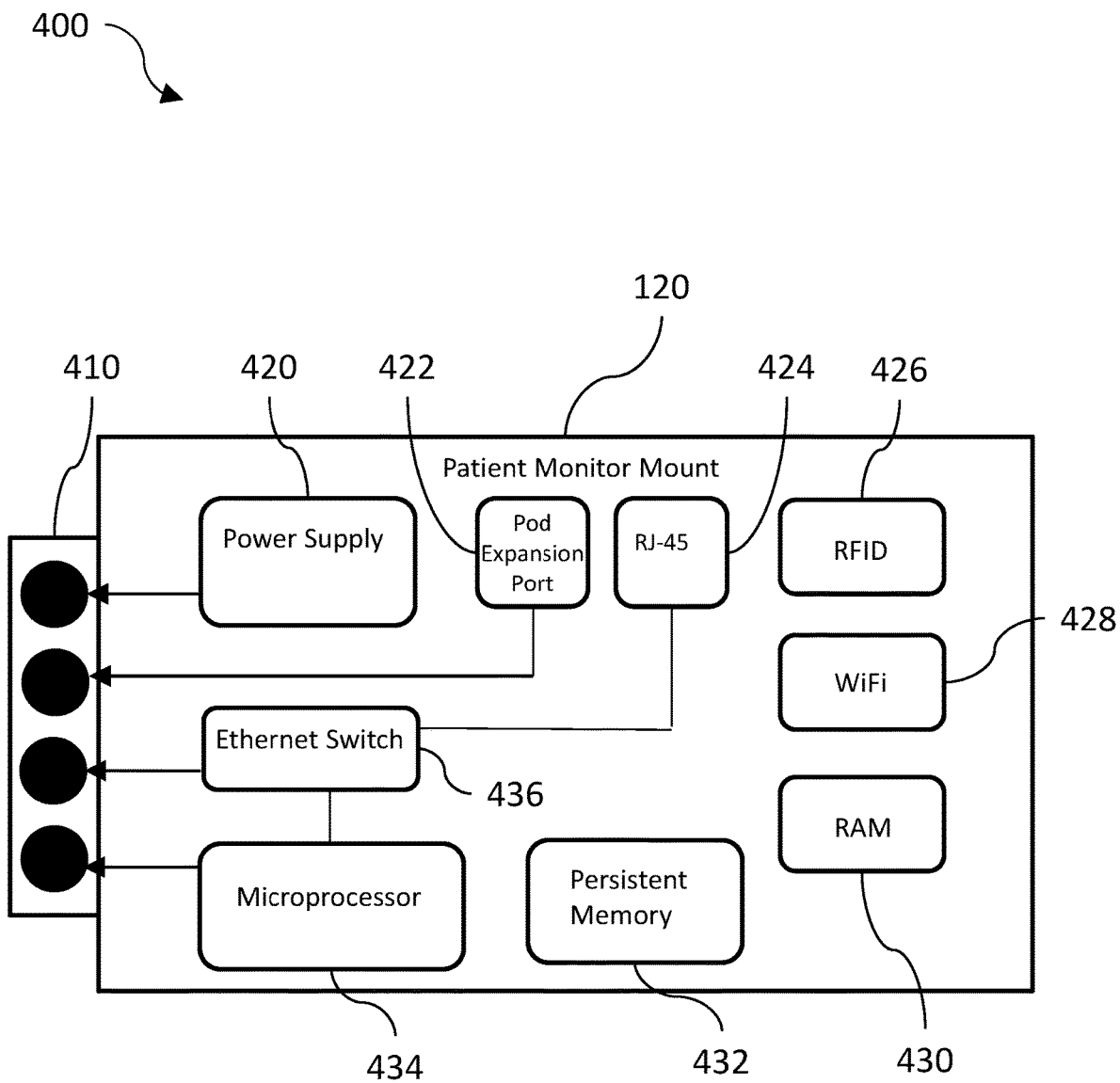
FIG. 4 is a diagram illustrating a hardware configuration of the patient monitor mount.

FIG. 4 is a diagram 400 illustrating a hardware visualization configuration 210 of the patient monitor mount 120. The patient monitor mount 120 can include a dock connector 410, a power supply 420, a pod expansion port 422, a registered jack 424, a radio-frequency identification (RFID) interface 426, a WiFi interface 428, a random-access memory 430, a persistent memory 432, a microprocessor 434, and an Ethernet switch 436. The patient monitor mount 120 can include any combination of the above elements as well as including additional elements as required to enable the functionality described in the application. The description of examples of alternate computer hardware components that can be used in lieu of, or in addition to, the components described below, can be found after the discussion of FIG. 5.

The dock connector 410 can be used to physically and/or electrically connect the patient monitor mount 120 to the patient monitor 110. The dock connector 410 can include snaps, tabs, threaded holes and screws, levers, etc. to create a physical connection between the patient monitor 110 and the patient monitor mount 120. The dock connector 410 can also include, e.g. exposed leads, tabs, plates, wires, etc. to enable the required electrical connections between the patient monitor 110 and the patient monitor mount 120.

The power supply 420 can be, e.g. a DC or AC power line/source from the building, or can be a battery power supply. The power supply 420 can also include transformers and/or physical couplers, e.g. 3-prong to 2-prong, 220 VAC to 120 VAC, etc. to allow the patient monitor mount 120 to connect to/from varying types of power outlets.

The pod expansion port 422 can allow various medical devices/physiological sensors to be coupled to the patient monitor.

The registered jack 424 can be any sort of network or electrical jack, e.g. RJ-11, RJ-45, coaxial threaded jack, BNC, LEMO, etc. The registered jack 424 can be used to allow the patient monitor mount 120 to transfer network signals from the network to the microprocessor and/or the patient monitor 110.

The RFID interface 426 can be used to enable RFID detection and tracking of the patient monitor mount 120. Each patient monitor mount 120 can have a unique RFID tag that identifies the patient monitor mount 120 to the network or other RFID reader. The RFID tag can be, e.g. active, passive, battery-assisted, etc.

The WiFi interface 428 can be any sort of transceiver that allows wireless communication between the patient monitor mount 120 and a WiFi transmitter, hotspot, wireless router, etc.

The random-access memory 430 can be used to store instructions executed by the microprocessor 434 during operation of the patient monitor mount 120.

The persistent memory 432 can be memory used to store visualization configurations 210 or other programming instructions for the patient monitor mount 120, e.g. flash memory, magnetic memory, etc.

The microprocessor 434 can be any sort of microprocessor and/or chipset that allows execution of programmed instructions for the patient monitor mount 120.

The Ethernet switch 436 can be any switching element that allows the registered jack to communicate with the patient monitor 110 and the microprocessor 434.

Figure 5:
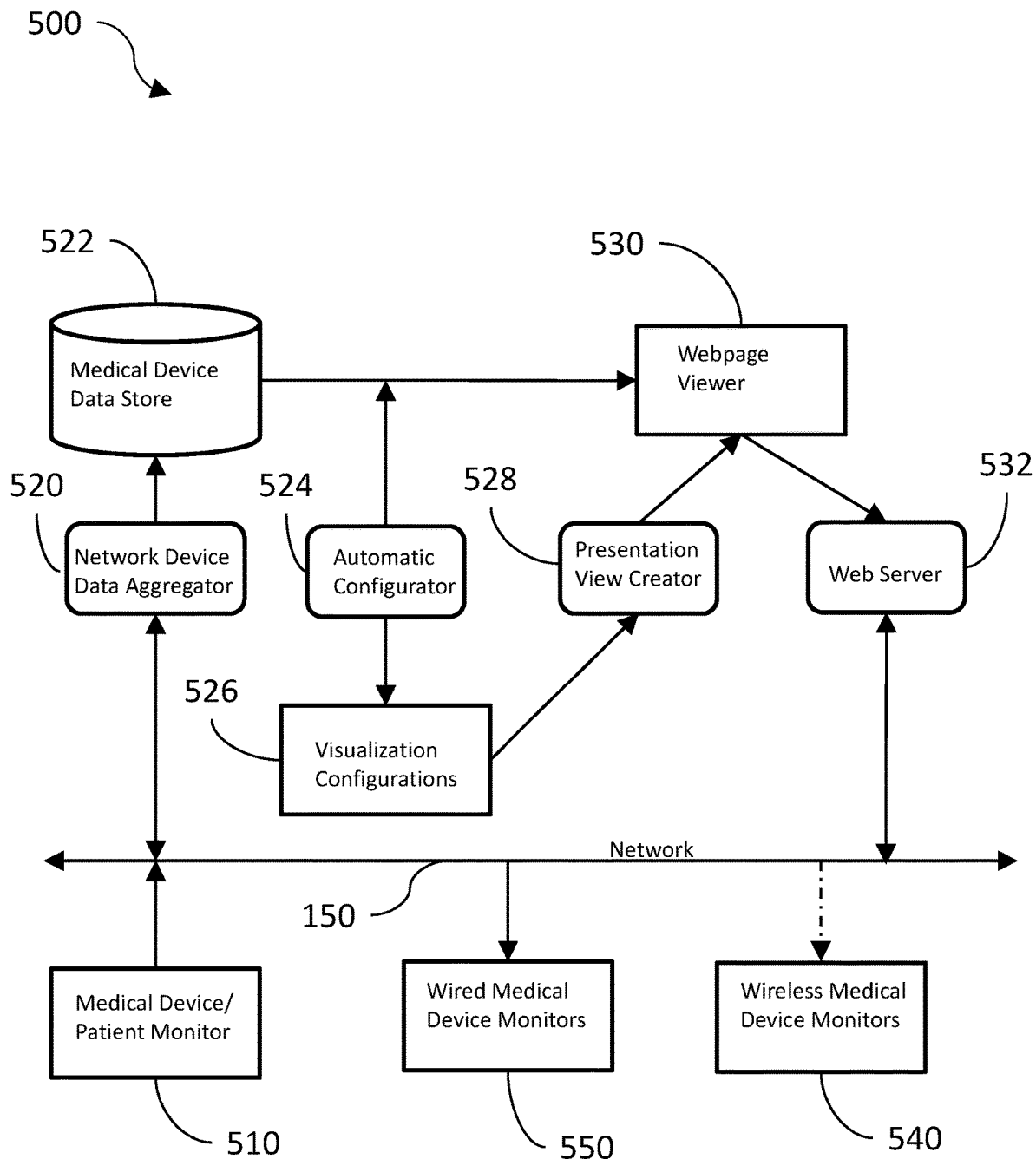
FIG. 5 is a system diagram illustrating the patient monitor mount connected to an information technology system.

FIG. 5 is a system diagram 500 illustrating the patient monitor mount 120 connected to the network 150. There can be multiple patient monitor mounts 120 connected throughout a healthcare facility, via the network 150. The network connectivity can allow the data 130 of the patient monitor 110 to be displayed at any web-enabled display. Also, caregivers can remotely view a medical procedure being performed on a patient connected to the patient monitor mount 120 according to their own stored visualization configuration 210, independent of the visualization configuration 210 of the caregiver(s) actually performing the procedure on the patient.

At 510, the patient can be connected to one or more medical devices 140, patient monitors 110, and/or patient monitor mounts 120. The devices, at the point-of-care, can be connected to a network via the patient monitor mount 120 or any other connection enabling device, e.g. a wired/wireless router.

At 520, there can be a network device data aggregator that compiles a list or other memory object that contains reference to all connected medical devices 140, patient monitors 110, and patient monitor mounts 120. It is not necessary that the detected medical devices 140 be connected to the patient monitor mount 120; any networked medical device 140 can be aggregated.

At 522, the list from the network device data aggregator at 520 can be stored in a medical device 140 data store. The medical device 140 data store can be, e.g. a database, a server, a cluster, etc. that collects information from the network device data aggregator and stores and organizes it for reference by other networked programs.

At 524, the automatic configurator can be a program responsible for deciding on the contents of the display based on what data is available the automatic configurator supports multiple canned visualization configurations 210 and can also support user-defined visualization configurations 210. In one implementation, unless a user changes it, the automatic configurator can provide a default display visualization configuration 210 that replicates the displayed data on the medical device 140. The automatic configurator can provide a visualization configuration 210 description of the webview layout to describe what images are being displayed to the user.

At 526, the automatic configurator can provide canned or user-generated visualization configurations 210. Also, the visualization configurations 210 can be shared between users and further customized by the current user of the visualization configuration 210.

At 528, the visualization configurations 210 from 526 can be sent to a presentation view creator. The presentation view creator can be a GUI (graphical user interface) or other development environment that allows the visualization configurations 210 to be customized before being displayed on the webview. The presentation view creator can include, e.g. providing lists of available visualization configurations 210, other medical devices 140 connected to the network 150, lists of diagnostic traces available through the medical devices 140 and the patient monitor mounts 120, etc.

At 530, the webpage viewer can be a webpage, JAVASCRIPT, or other end-user GUI that can display the view created at 528. The webpage viewer can be used to proof the webviews and display how they will be shown to anyone viewing the webview on their internet browser.

At 532, the webpage viewer can export webviews to a web server. The web server can be any computer, server, database, etc. that distributes the webviews to the network. The web server can distribute the webviews to connected devices automatically, or in response to user request.

At 540 and 550, webviews can be downloaded to network connected medical device 140 monitors wirelessly or wired, respectively. The medical device 140 monitors can be, e.g. large screen TV's, computer monitors, terminals, etc. that can then display the requested visualization configuration 210 of medical device 140 diagnostic traces.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

The invention claimed is:

1. A method comprising:
storing, in a patient monitor mount, customized visualization configurations in association with a device rule set configured to govern conflicts between two or more medical devices and, responsive to an event of conflict, to determine based upon the device rule set which of the two or more medical devices will display data on a patient monitor communicating with the patient monitor mount;
receiving, by the patient monitor mount, data from at least one medical device of the two or more medical devices monitor mount, the patient monitor mount comprising being separate and distinct from the at least one medical device;
monitoring, by the patient monitor mount and in response to the data received from the at least one of the two or more medical devices, for a conflict between the two or more medical devices;
determining, by the patient monitor mount and based on the monitoring, that the conflict between the two or more medical devices has occurred;
generating, by the patient monitor mount in response to the determination and by using the device rule set, at least one command to transmit to a visualization device that upon receipt at the visualization device causes a visualization on the visualization device to change; and
transmitting, by the patient monitor mount to the visualization device, the generated at least one command.

2. The method according to claim 1, wherein the change in visualization is triggered based on the device rule set comprising device rules specifying which, if any, visualizations should be rendered on the visualization device in response to the conflict.

3. The method according to claim 1, wherein the patient monitor mount comprises:
a dock connector enabling a mechanical and electrical connection between the patient monitor and the patient monitor mount,
a random-access memory capable of storing machine-readable instructions,
a persistent memory capable of storing non-transient machine-readable instructions, and
a microprocessor operably connected to the dock connector, the microprocessor capable of accessing the random-access memory and the persistent memory for executing programmed instructions.

4. The method according to claim 1, wherein the command is an HTML command.

5. The method according to claim 1, wherein the customized visualization configuration comprises:
a list containing a plurality of diagnostic traces;
priority information of the plurality of diagnostic traces for displaying;
positions of the plurality of diagnostic traces on the patient monitor; and
display preferences of the plurality of diagnostic traces.

6. The method according to claim 1, wherein data displayed on the visualization device upon receipt of the at least one command is replicated on a display of a computer connected to a network.

7. The method according to claim 6, wherein the connection is a wired connection.

8. The method according to claim 6, wherein the connection is a wireless connection.

9. The method according to claim 3, wherein the patient monitor mount further comprises:
a power supply operably connected to the dock connector to provide power to the patient monitor mount;
a pod expansion port operably connected to the dock connector;
a registered jack operably connected to the dock connector to enable internet communication with the patient monitor mount;
an RFID interface to enable RF communication with the patient monitor mount;

a WiFi interface to enable wireless communication with the patient monitor mount; and an Ethernet switch, operably connected to the dock connector, the microprocessor, and the registered jack.

10. The method according to claim 1, wherein the visualization device is at least one of a terminal, a wall monitor, a mobile device, a desktop monitor, or dedicated LCD display.

11. The method according to claim 1, wherein the visualization device is remote and distinct from both the patient monitor mount and the patient monitor.

12. An apparatus, comprising:
a patient monitor mount, the patient monitor mount including:
a processor;
a memory communicating with the processor, the memory storing:
a device rule set determining a set of medical data to be displayed from a particular medical device among a plurality of medical devices is displayed, the determining including resolution in the event of a conflict between at least two of the medical devices; and
a set of instructions that, when executed by the processor, perform a method comprising:
receiving medical data from the plurality of medical devices;
determining that the conflict is present;
resolve the conflict to determine which conflicting medical device presents the medical data received therefrom on a visualization device; and
transmitting a command to the visualization device that, upon receipt, causes the visualization device to display a visualization of the medical data from the determined conflicting medical device.

13. The apparatus of claim 12, wherein the patient monitor mount is fixed to a treatment location.

14. The apparatus of claim 12, wherein
the patient monitor mount further comprises a dock connector enabling a mechanical and electrical connection between the patient monitor and the patient monitor mount;
the processor is a microprocessor;
the memory includes:
a persistent memory capable of storing non-transient machine-readable instructions; and
a random-access memory capable of storing machine-readable instructions; and
the processor is operably connected to the dock connector and capable of accessing the random-access memory and the persistent memory for executing the programmed instructions to perform the method.

15. The apparatus of claim 14, wherein the patient monitor mount further comprises:
a power supply operably connected to the dock connector to provide power to the patient monitor mount;
a pod expansion port operably connected to the dock connector;
a registered jack operably connected to the dock connector to enable internet communication with the patient monitor mount;
an RFID interface to enable RF communication with the patient monitor mount;
a WiFi interface to enable wireless communication with the patient monitor mount; and
an Ethernet switch, operably connected to the dock connector, the microprocessor, and the registered jack.

16. The apparatus of claim 12, further comprising the plurality of medical devices.

17. The apparatus of claim 12, wherein the patient monitor mount and the plurality of medical devices communicate over a network.

18. The apparatus of claim 15, wherein the patient monitor mount and the plurality of medical devices communicate over the network with a plurality of wired connections, a plurality of wireless connections, or a combination of wired connections and wireless connections.

19. The apparatus of claim 12, wherein the patient monitor mount and one or more of the plurality of medical devices communicate wirelessly.

20. The apparatus of claim 12, wherein the patient monitor mount and one or more of the plurality of medical devices communicate over a wired connection.

21. The apparatus of claim 12, further comprising the visualization device.

22. The apparatus according to claim 21, wherein the visualization device is at least one of a terminal, a wall monitor, a mobile device, a desktop monitor, or dedicated LCD display.

23. The apparatus according to claim 21, wherein the visualization device is remote and distinct from both the patient monitor mount and the patient monitor.

24. The apparatus according to claim 12, wherein the command is an HTML command.

25. The apparatus according to claim 12, wherein the customized visualization configuration comprises:
a list containing a plurality of diagnostic traces;
priority information of the plurality of diagnostic traces for displaying;
positions of the plurality of diagnostic traces on the patient monitor; and
display preferences of the plurality of diagnostic traces.

* * * * *